United States Patent
Webster et al.

(10) Patent No.: US 12,172,378 B1
(45) Date of Patent: Dec. 24, 2024

(54) METHOD AND SYSTEM OF CONTROLLING CELL FUNCTIONS ON 3D PRINTED AND 3D MANUFACTURED MATERIALS MODIFIED WITH LIPASES

(71) Applicant: PrinterPrezz, Inc., Fremont, CA (US)

(72) Inventors: Thomas Webster, Lviv, RI (US); Christopher Dang, Berkeley, CA (US); Aditya Prakash Morey, Freemont, CA (US); Dylan Tepper, Hayward, CA (US)

(73) Assignee: Zeda Holdings, Inc., Fremont, CA (US)

( * ) Notice: Subject to any disclaimer, the term of this patent is extended or adjusted under 35 U.S.C. 154(b) by 375 days.

(21) Appl. No.: 17/526,648

(22) Filed: Nov. 15, 2021

(51) Int. Cl.
| | | |
|---|---|---|
| *B28B 1/00* | (2006.01) | |
| *B28B 11/00* | (2006.01) | |
| *B28B 11/22* | (2006.01) | |
| *B29C 64/147* | (2017.01) | |
| *B29C 64/30* | (2017.01) | |
| *B29C 64/35* | (2017.01) | |
| *B33Y 10/00* | (2015.01) | |

(Continued)

(52) U.S. Cl.
CPC .............. *B29C 64/30* (2017.08); *B28B 1/001* (2013.01); *B28B 11/00* (2013.01); *B28B 11/22* (2013.01); *B29C 64/147* (2017.08); *B29C 64/35* (2017.08); *B33Y 10/00* (2014.12); *B33Y 40/20* (2020.01); *B29L 2031/7532* (2013.01); *B33Y 80/00* (2014.12)

(58) Field of Classification Search
CPC ....... B28B 1/001; B28B 11/22; B29C 64/147; B29C 64/35
See application file for complete search history.

(56) References Cited

U.S. PATENT DOCUMENTS

2012/0288699 A1* 11/2012 Ahlberg .................. A61L 24/00
428/323
2016/0361472 A1* 12/2016 Neilan ..................... A61L 31/14
(Continued)

FOREIGN PATENT DOCUMENTS

WO WO-2023027974 A1 * 3/2023

OTHER PUBLICATIONS

AAT Bioquest "Potassium Phosphate (pH 5.8 to 8.0) Preparation and Recipe" via https://www.aatbio.com/resources/buffer-preparations-and-recipes/potassium-phosphate-ph-5-8-to-8-0 (Year: 2022).*

*Primary Examiner* — Binh X Tran
(74) *Attorney, Agent, or Firm* — Staniford Tomita LLP

(57) ABSTRACT

Implantable devices having rougher surfaces and more surface area can be made of polymers such as PEEK or PAEK using a 3D printing process. The 3D implantable devices can be soaked in a lipase solution to etch the surface which can alter the surface energy, surface roughness, and atomic composition. After the lipase solution soaking, the 3D printed implantable devices can be removed from the solution and thoroughly rinsed with a cleaning fluid such as an acetone solution. The outer surfaces of the lipase treated 3D printed implantable device can also be surface activated by UV light or other photocatalytic activity to decrease bacteria attachment and growth. The surface energy of the resulting 3D printed implantable devices enhances patient ingrowth resulting in a faster recovery.

17 Claims, 11 Drawing Sheets

Lipase Treated: RMS 113.09 nm

(51) Int. Cl.
*B33Y 40/20* (2020.01)
*B29L 31/00* (2006.01)
*B33Y 80/00* (2015.01)

(56) References Cited

U.S. PATENT DOCUMENTS

2017/0239719 A1* 8/2017 Buller ................ B22F 12/49
2020/0238751 A1* 7/2020 Webster ............. A61M 16/04

* cited by examiner

SLS PEEK

Control: RMS 33.01 nm

Lipase Treated: RMS 63.05 nm

FFF PEEK

Control: RMS 13.09 nm

Lipase Treated: RMS 113.09 nm

SLS PEEK

Control: RMS 26.81 nm

Lipase Treated: RMS 132.55 nm

PEEK Machined

Control: RMS 42.1 nm

Lipase Treated: RMS 148.76 nm

RMS = 4.024 nm

FFF PEEK

PEEK Machined    FIG. 11

METHOD AND SYSTEM OF CONTROLLING CELL FUNCTIONS ON 3D PRINTED AND 3D MANUFACTURED MATERIALS MODIFIED WITH LIPASES

BACKGROUND 3D printing provides a system and method for creating metal, polymer, and ceramic structures that have significantly altered geometric shapes compared to conventional 2D manufacturing methods. 3D printing has also been used to create medical implant devices that can be surgically implanted into the patient. Once implanted, the patient's body can integrate the implant device at the implant location. The body can grow onto the surface of the implant device and ideally the implant will not lead to infection. However, there have been problems with body ingrowth into the implant devices and infections at the body locations for the implant devices. What is needed is an improved implant device apparatus and method that increases the rate of body ingrowth on the implant device that also reduces the likelihood and rate of infection.

SUMMARY OF THE INVENTION

The present invention is directed towards an improved implant device apparatus and method that has a surface that increases the rate of body ingrowth on the implant device that also reduces the likelihood and rate of infection compared to prior implant devices. In some embodiments, the initial implant structure can be fabricated from 3D printing a base material which can be a metal, polymer, ceramic, or other suitable materials. Once formed by 3D printing, the initial implant structure can be exposed to a lipase or enzyme that changes the chemistry and roughness of the surface of the implant device, collectively changing its surface energy. The 3D printed implantable devices can include: hip implant, shoulder implant, ankle implant, foot implant, knee implant, joint implant, vascular stent, pacemaker or pacemaker component, sutures, neural probe, intraocular lens, spinal cage, pedicle screw, interbody spinal device, drug delivery device, micron particle, nano particle, urethral stent, catheter, endotracheal tube, or any material inserted in the body.

In some embodiments, the chemistry and roughness of the surfaces of 3D printed fabricated implant structures can be changed by soaking the implant structure in a lipase solution that includes *Rhizopus arrhizus*. *Rhizopus arrhizus* is a fungus of the family Mucoraceaelipase which produces a lipase that can degrade certain materials and biomolecules. Lipases, much like other enzymes, can break bonds of the materials they contact and interact with. Typically, these broken bonds result in higher surface energy due to the increased exposure of electrons, but higher surface energy does not always have to be the case. The implant lipase soaking process can be carefully controlled by altering the type of lipase, concentration of lipase, time of lipase exposure (such as in soaking), temperature and pressure of exposure of the lipase, and so on. Since lipases are electrically charged, the lipase treatment process depends greatly on the surface properties of the underlying substrate that is to be modified. For example, surfaces with higher surface energy can have higher interaction levels with more highly charged lipases, and conversely, lower surface energy can have lower interaction levels with lower charged lipases.

In some embodiments, the 3D printed implantable device was soaked in a lipase solution at room temperature and ambient pressure for a predetermined period of time. For example, in an embodiment, the lipase solution can include a lipase at a concentration between about 0.0001-1.00 mg/ml of *Rhizopus arrhizus* or any other lipase material in a liquid which can be water. In other embodiments, the liquid can be a saline solution like phosphate buffered saline, tryptic soy broth, Luria broth, ethanol, acetone, cyclohexane, benzene, methanol, chloroform, tetrachloroethylene, pentane, and toluene. The other lipase solution soaking process conditions can be at room temperature under ambient pressure for a time period of 24 hours. In other embodiments, the lipase solution soaking process can occur at a temperature between about 1.7 degrees C. and 95 degrees C. The predetermined duration of the lipase solution soaking process can be between about 1 hour and 7 days. Afterwards, the lipase solution soaking in the 3D printed implantable devices can be removed from the solution and thoroughly rinsed with a cleaning fluid such as an acetone solution. The outer surfaces of the lipase treated 3D printed implantable device can also be surface activated by UV light or other photocatalytic activity to decrease bacteria attachment and growth.

Other embodiments could include lipases secreted by the following microorganisms or present in the following organs: *Aspergillus niger*, *Candida rugosa*, porcine pancreas, wheat germ, *Rhizopus oryzae*, *Aspergillus oryzae*, *Rhizopus niveus*, *Mucor miehei*, *Pseudomonas cepacia*, *Pseudomonas* sp., mammalian cells, *Mucor javanicus*, *Candida antarctica*, *Candida* sp., bovine milk, human pancreas, Pancreatin lipase, Amano Lipase A from *Aspergillus niger*, Lipoprotein Lipase from *Burkholderia* sp., Amano Lipase from *Pseudomonas fluorescens*, Amano Lipase PS, *Aspergillus oryzae*, Amano Lipase M from *Mucor javanicus*, Lipoprotein Lipase from *Pseudomonas* sp., *Chromobacterium viscosum*, Lipase A *Candida antarctica*, recombinant from *Aspergillus oryzae*, and Amano Lipase PS from *Burkholderia cepacia*.

The present invention is directed towards improving the surface properties of 3D printed and/or other 3D manufactured implantable material structures through exposure to lipases to change surface chemistry and create biologically-inspired nanometer surface features. In some embodiments, the lipase treatments can increase the surface area of the implant structure and thus alter the surface energy of the initial 3D printed material structures to between about 35 and 55 millinewton per meter (mN/m). Untreated 3D printed implant structures can have a much lower surface energy which can be less than 33 mN/m. 2D conventional manufactured implant surfaces can also have much lower surface energy which can be less than 22 mN/m which is a lower surface energy than untreated 3D printed implant structures and 3D printed implant structures that have received lipase treatment.

The ingrowth characteristics and the infection resistance of the implant structure can benefit from a higher surface energy. It has been found that 3D printed implant structures that have received lipase treatment raise the surface energy to about 35-55 mN/m and have both faster rates of bodily ingrowth and lower growth rates of infections than implant structures that have not received the lipase treatment and have a surface energy of less than 33 mN/m.

In an embodiment, the surface energy can be altered to an optimum value of about 42.5 millinewton per meter (mN/m) which is about the same surface energy as three proteins known to decrease bacteria colonization: casein, mucin, and lubricin. The surface energy of about 42.5 mN/m is also about the same as two proteins vitronectin and fibronectin that are known to promote the attachment and growth of osteoblasts. In other embodiments, the 3D printed implantable metals and polymers can reduce bacteria colonization and improve osteoblast ingrowth when the surface energy is within the range of about 33 to 47 mN/m. The present invention may improve the recovery process by having surface energies that match the surface energy of proteins known to decrease bacteria colonization and promote the attachment and growth of osteoblasts. The higher osteoblast ingrowth can improve the regeneration of bone, cartilage, ligaments, tendons, GI tissue, vascular tissue, cardiovascular tissue, skin, nervous system tissue, spinal tissue, muscle, or any tissue in the body.

As discussed, the initial surface energy of the 3D printed implant structure can be much different than the optimal surface energy of about 35-55 mN/m. 3D printed implants or 3D manufactured implants have a textured surface that has significantly greater surface area, surface exposure of chemistry, altered crystallinity, and altered mechanical properties compared to conventional 2D surfaces even of the same implant structure materials and chemistry. Thus, the surface energy of a 3D printed implant structures can be altered in a significantly different way compared to 2D fabricated structures by exposure to lipases.

Depending on the material to be exposed to the lipase, the underlying and exposed surface energy can be transformed to be more hydrophobic (low surface energy) or hydrophilic (high surface energy). All materials have surface energy due to broken bonds at their surfaces and bonding mechanisms used between atoms in that material. Generally, polymers have much lower surface energy than metals since polymers use covalent bonds (or equal sharing of electrons) as opposed to metallic bonds or ceramics which use ionic bonding (or unequal sharing of electrons). Electrons are charged particles, so the more electrons at the surface of a material, the higher their surface energy. Lipase soaking can not only change the chemistry of the underlying implant material during exposure by breaking bonds and exposing the implant material to new chemistries, but lipase soaking can also change the surface roughness, in which both chemistry and roughness alter implant surface energy. The new increased roughness on the surface of the lipase treated implant device can significantly promote the exposure of the new implant chemistry and, thus, lipase exposure can increase the presence of charged electrons more than micron structured or flat surfaces of non-processed surfaces. If done correctly, this significantly higher exposure of charged electrons can significantly increase implant surface energy. Lipase exposure can increase surface energy by changing implant chemistry to that of a higher energy, increasing surface area of that new chemistry, creating new textures, developing increased roughness, changing crystallinity, and creating thicker layers of a new chemistry. Conversely, if lipase exposure created an implant to have a new lower surface energy chemistry, it would decrease overall material surface energy.

3D printing generally has a more porous and higher surface area surface finish than traditional fabrication methods such as milling, casting, molding, computer numerical control (CNC), etc. Because the surfaces of 3D printed structures and other 3D manufactured materials can have a higher surface roughness, the surface energy of 3D implant structures can be higher than the surface energy of implant structures made with more traditional fabrication methods. 3D printed implant devices that have also been surface processed through lipase exposure can have improved implant characteristics including a surface energy between about 35 and 55 mN/m that are superior to non-lipase exposed implant devices that have lower surface energies.

Initial protein interactions when adsorbed onto implantable devices are well known to control bacteria and mammalian cell (such as osteoblast) adhesion, proliferation, and if appropriate, extracellular matrix deposition (such as bone). This is because proteins contain amino acids which by charge attract select cell membrane receptors in cells to encourage their adhesion and subsequent functions. Since proteins are composed of diverse amino acids with different charges, proteins themselves possess different charges whose adsorption and bioactivity can be controlled by altering implant 3D printed chemistry and nanotexture by ALD processing. By altering nano textures on the implant surfaces of the implant devices to increase surface area exposure of a charged material, one can change surface energy to in turn alter protein adsorption and to in turn inhibit or promote cell interactions.

One well-established method to measure changes in surface energy is to determine contact angles with liquids of different surface tensions and compare the surface energy of implants to key proteins known to inhibit bacteria and/or promote mammalian cell interactions. Importantly, three proteins known to decrease bacteria colonization have surface energies around 42.5 mN/m (casein, mucin, and lubricin). Moreover, two proteins known to promote the attachment and growth of osteoblasts also have surface energies around 42.5 mN/m (vitronectin and fibronectin). By exposing 3D printed implant devices to lipases, the surface energy can be optimized to both inhibit bacteria and promote mammalian cell interactions.

The premise of this invention is that lipase exposure can alter the surface energy of 3D printed and other 3D manufactured materials and in a much different way than on traditional 2D manufactured materials to inhibit bacteria and promote osteoblast function to improve implant performance.

DETAILED DESCRIPTION

Figure 1:
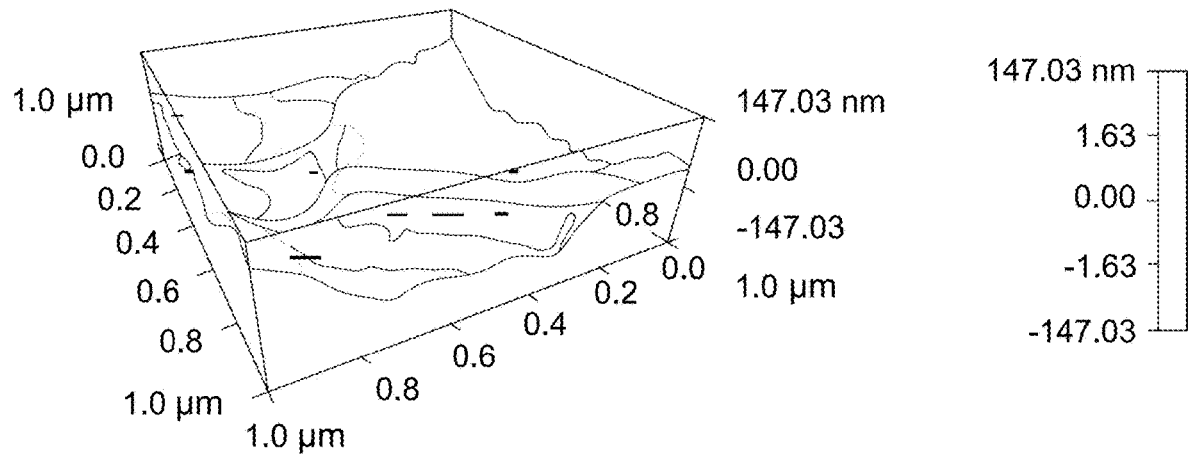
FIG. 1 illustrates an AFM analysis of SLS 3D printed PEEK polymers before lipase etching.

The present invention is directed towards a method for making 3D implantable devices such as: hip implant, shoulder implant, ankle implant, foot implant, knee implant, joint implant, vascular stent, pacemaker or pacemaker component, sutures, neural probe, intraocular lens, spinal cage, pedicle screw, interbody spinal device, drug delivery device, micron particle, nano particle, urethral stent, catheter, endotracheal tube, or any material inserted in the body. The 3D implantable devices can then be soaked in a lipase solution to etch the surface which can alter the surface energy, surface roughness, and atomic composition. Afterwards, the lipase solution soaking the 3D printed implantable devices can be removed from the solution and thoroughly rinsed with a cleaning fluid such as an acetone solution. The outer surfaces of the lipase treated 3D printed implantable device can also be surface activated by UV light or other photocatalytic activity to decrease bacteria attachment and growth.

3D Printed Samples: 3D printing uses heat to bind metal, polymer, ceramic, or composite particles or other fundamental building blocks such as powdered particles, filament, layers, groups of particles together in a pre-programmed manner to build structures with controllable porosity, surface features, textures, roughness, thickness, and geometries. As such, compared to conventional 2D material manufacturing techniques (such as cast-molding, heat forging, cutting, forging, welding, stamping, etc.), 3D printing can manufacture materials with very unique physical characteristics, such as nanoscale and micron porosity, unique pore structures, controllable surface features, greater mechanical properties, altered crystallinity, higher surface energy, etc.).

Examples of possible 3D printed metals to create the implant structures include: titanium, Ti6Al4V, stainless steel, nitinol, CoCrMo, Mg, selenium, etc. Examples of possible polymers used to create the implant structures include: poly-ether-ether-ketone, polyurethane, polyethylene, polypropylene, polystyrene, PDMS, poly-ether-ketone-ketone, poly-lactic acid, poly-glycolic acid, poly-lactic-co-glycolic acid, poly-vinyl chloride, etc. Examples of possible ceramics used to create the implant structures include: calcium phosphates, hydroxyapatite, metal oxides, alumina, etc. Examples of composites include any combination of the above.

In one embodiment, selective laser sintering (SLS) 3D printing can be used in which polymer powder (such as PAEK or PEEK) is loaded into the 3D printer. A laser can be used as a power source to sinter the powdered polymer material. The SLS 3D printer can aim the laser at points in a space as defined by a 3D model, binding the polymer powder material together to create a solid structure. In some embodiments, the following processing conditions are followed: chamber temperature between about 200-350 degrees C., build platform and frame temperature between about 200-350 degrees C., hatching laser power=7-20 W, hatching laser speed between about 1000-4,000 mm/s, contour laser power between about 1-10 W, and contour laser speed between about 500-2,000 mm/s.

In other embodiments, fused filament fabrication (FFF) or otherwise known as fused deposition modeling (FDM) can be used to create 3D printed structures. The polymer filament is fed from a large spool through a moving, heated printer extruder head, and the melted filament is deposited on the growing printed structure. The print head is moved under computer control to define the printed shape. Usually the head moves in two dimensions to deposit one horizontal plane, or layer, at a time, the work or the print head is then moved vertically by a small amount to begin a new layer. For FFF/FDM fabrication, the following processing conditions can be used: temperature between about 200 and 500 degrees C. and a filament speed between about 10-1,000 mm/s.

In order to quantify the benefits of 3D printed structures compared to conventional 2D manufactured structures, testing was performed to compare the performance characteristics. Polymer test samples were made of polymers (such as PEEK) and were manufactured using conventional 2D fabrication processes. For example, 2D processing of polymers can be extruded PEEK bar stock or soluble polymers placed in molds then allowed to cure (or solidify). Computer numerical control (CNC) machining, which is a subtractive process, can also be used to build 3D polymer structures. For the described experiments, the 2D fabricated test samples were manufactured by Invibio Biomaterial Solutions. In order to accurately compare the performance of the 3D printed and 2D manufactured structures, each of the test samples were exposed to the same lipase etch processing.

Lipase Etch: 3D printed, 3D manufactured (CNC), and 2D conventional manufactured polymers were soaked in a 0.1 mg/ml *Rhizopus arrhizus* liopase solution for 24 hours at room temperature which can be between about 10° C. and 30° C. under ambient pressure. Samples were then thoroughly rinsed with an acetone solution before the performance characteristics were measured.

In some embodiments, after the lipase etching, the 3D printed implantable devices can be removed from the solution and thoroughly rinsed with a cleaning fluid such as an acetone solution. The outer surfaces of the lipase treated 3D printed implantable device can also be surface activated by UV light or other photocatalytic activity to decrease bacteria attachment and growth.

Material Characterization: Samples were characterized for surface energy using contact angles and following the Owen-Wendt equation as described below, topography using atomic force microscopy (AFM; Zeiss Supra 55VP) and chemistry using X-ray Photoelectron Spectroscopy (XPS; Physical Electronics VersaProbe II). Samples were also tested for a change in mechanical properties by means of compressive and tensile testing using the Instron 3382A 100 KN Universal testing machine.

For contact angles, the surface energy of the samples of interest was determined using standard contact angle measurements. For this, a Phoenix 150 Contact Angle Analyzer was used in a three-solvent system with deionized water, ethylene glycol, and glycerol. For some of the experiments, mucin (0.1 mg/ml), casein, and vitronectin (50 µg/ml) were added to water droplets. Mucin and casein are proteins that reduce bacteria function and vitronectin increases osteoblast functions. Thus, lower contact angles for these proteins would indicate greater interactions of these proteins with the samples, implying decreased bacteria and increased osteoblast functions on those same samples. A 16 µl drop per solvent was dropped onto the sample surfaces in triplicate for each sample and images were obtained after 2 seconds. Contact angles were measured using the DropSnake plugin on Fiji. The surface energy of each substrate was determined by applying the Owens/Wendt theory in tandem with contact angle data and solvent surface tension values, of which the latter were obtained from the literature. The Owens/Wendt model structurally follows the mathematical formulation shown in Equation I below, where $\sigma_L^D$ and $\sigma_L^P$ are the dispersive and polar components, respectively, of the wetting liquid's surface tension, and where θ is the contact angle that the solvent makes with the substrate surface.

Owens/Wendt theory $$\frac{\sigma_L(\cos\theta + 1)}{2(\sigma_L^D)^{1/2}} = (\sigma_S^P)^{1/2} \frac{\sigma_L^{P1/2}}{\sigma_L^{D1/2}} + (\sigma_S^D)^{1/2}. \qquad \text{Equation I}$$

Mechanical Properties: Mechanical strength properties of the test samples were measured by means of compressive testing using the Instron 3382A 100 KN Universal testing machine. A 100 kN non hydraulic Instron machine was used with compressive testing fixtures at a strain rate of 12 mm/min with the end of test criteria being a displacement of 7.5 mm at room temperature which can be between about 10° C.-30° C.

Osteoblast Adhesion: 2,500 hFOB (human fetal osteoblasts; ATCC CRL-11372) cells/ml of a media suspension were placed onto each test sample in cell culture plates in DMEM plus 10% fetal bovine serum and 1% of penicillin-streptomycin. All plates were incubated in a humidified environment under 5% $CO_2$ and 37° C. for 4 hours. At the completion of the incubation time, the samples were carefully transferred to new plates and immersed in a 16.7% v/v MTS [3-(4,5-dimethylthiazol-2-yl)-5-(3-carboxymethyl phenyl)-2-(4-sulfophenyl)-2H-tetrazolium, inner salt; Promega] solution (1 ml MTS: 5 ml DMEM-F12). Test specimens in MTS were incubated in a humidified atmosphere at 5% $CO_2$ and 37° C. After reduction of the tetrazolium compound, the bulk solutions surrounding each test specimen were re-suspended through continuous pipetting to ensure homogeneity in color saturation, and 200 µl from each solution was deposited into the wells of clear bottom 96-well plates. Absorbance readings at λ equal to 490 nm (which detects the formazan dye that is generated when the MTS tetrazolium compound is reduced by viable cells) were immediately obtained using a spectrophotometer. All procedures involving MTS were performed in the dark to avoid the discoloration of the reagent due to light-sensitivity. MTS procedures were performed on three replicates of each sample type.

MRSA Colonization: Methicillin resistant *Staphylococcus aureus* (MRSA; ATCC BAA-1717) was inoculated ($10^6$) on the surfaces for 24 hours. For this, the bacteria were rehydrated in 6 mL of Luria broth (LB) consisting of 10 g tryptone, 5 g yeast extract, and 5 g NaCl per liter double distilled water with the pH adjusted to 7.4 (all chemicals obtained from Sigma Aldrich, St. Louis, MO, USA). 10% fetal bovine serum (FBS; Hyclone) was added to the LB to more accurately represent real body fluids. The bacteria solution was agitated under standard cell conditions (5% $CO_{2/95}$% humidified air at 37° C.) for 24 hours until the stationary phase was reached. The second passage of bacteria was diluted at a ratio of 1:200 into fresh LB supplemented with 10% FBS and incubated until reaching the stationary phase. The second passage was then frozen in one part LB and 10% FBS and one part glycerol (Sigma Aldrich) and stored at −18° C. All experiments were conducted from this frozen stock. One day before bacterial seeding for experiments, a sterile 10 µl loop was used to withdraw bacteria from the frozen stock and to inoculate a centrifuge tube with 3 mL of fresh LB supplemented with 10% FBS. At the end of 24 hours, standard colony forming units were determined using the standard spreading and plating method.

Statistical Analyses: All cell experiments were run in triplicate and repeated a minimum of three times per substrate type. Numerical data were analyzed using Analysis of Variance (ANOVA); values of $p<0.05$ were considered significant. Duncan's multiple range tests were used to determine differences between means.

Test Results: Untreated 3D printed control samples and 3D printed samples treated with the lipase were characterized by surface energy (Table 1), mechanical properties (Table 2), AFM (FIGS. 1 and 2), XPS (FIGS. 3 and 4), MRSA colonization (FIG. 5), and osteoblast adhesion (FIG. 6). Collectively, results showed that first 3D printed and 3D manufactured polymers behaved differently and have different physical characteristics than conventional 2D polymers. 3D printed polymers are known to have altered crystallinity which can change surface energy to interact different with lipases. The lipase exposure also increased the nanoscale roughness of the 3D printed and 3D manufactured polymers which significantly increased surface energy to optimally interact with proteins known to decrease MRSA colonization (such as mucin and casein as demonstrated by their generally lower contact angles when containing such proteins), decreased MRSA colonization, and increased osteoblast adhesion compared to control non-lipase exposed 3D printed and manufactured polymers. Moreover, results showed that 3D printing the polymers increased roughness as assessed by AFM, changed surface chemistry, increased surface energy, decreased MRSA and increased osteoblast adhesion compared to traditional 2D manufactured polymers.

TABLE 1

| Samples | Surface Energy (mJ/m$^2$) | Mucin Containing Contact Angle (Degree) | Casein Containing Contact Angle (Degree) | Vitronectin Containing Contact Angle (Degree) |
|---|---|---|---|---|
| Control SLS 3D PAEK Printed | 42.2 | 60.33 | 60.35 | 57.57 |
| Lipase SLS 3D PAEK Etched | 73.68 | 27.47 | 47.47 | 24.77 |
| Control SLS 3D PEEK Printed | 40.06 | 46.63 | 70.74 | 69.44 |
| Lipase SLS 3D PEEK Printed | 77.91 | 48.72 | 51.42 | 49.65 |
| Control FFF 3D PEEK Printed | 32.42 | 49.01 | 75.17 | 76.19 |
| Lipase FFF 3D PEEK Printed | 39.41 | 42.77 | 67.69 | 56.39 |
| Control Machined 3D PEEK | 41.01 | 50.75 | 69.00 | 59.73 |
| Lipase Machined 3D PEEK | 35.61 | 58.02 | 55.62 | 64.76 |

Table 1 includes the Contact Angles and Surface Energy of Lipase Etched 3D Printed Materials. As a comparison, 2D traditionally manufactured PEEK (fabricated by Invibio) had a surface energy of 24.9 mJ/square m demonstrating significantly higher surface energy for any of the 3D printed PEEK samples. Note: Mucin and casein are antibacterial proteins and vitronectin is a pro-bone growing protein.

As shown in Table 1, the surface energy difference between the 2D PEEK control (24.9 mJ/square m) v. Control FFF 3D PEEK Printed (32.42 mJ/square m) and Control Machined 3D PEEK (41.01 mJ/square m) is 7.52 and 16.11 mJ/square m, respectively. These are significant differences that resulted from changes in roughness (FIGS. 1 through 9) and chemistry (FIGS. 10 through 14).

Moreover, the surface energy difference between the Control SLS 3D PAEK Printed (42.2 mJ/square m) v. Lipase SLS 3D PAEK Printed (73.64 mN/m) is 31.44 mJ/square m. The surface energy difference between the Control FFF 3D PEEK Printed (32.42 mJ/square m) v. Lipase FFF 3D PEEK 3D Printed (39.41 mJ/square m) is 6.99 mJ/square m. These are significant differences that resulted from changes in roughness (FIG. 1 through 9) and chemistry (FIGS. 10 through 14).

As shown in Table 2, 3D printed polymers have much different compressive modulus than conventional 2D polymers. This provides significant evidence that 3D printed polymers have much different properties than 2D polymers.

TABLE 2

| Samples | Compressive Young's Modulus (MPa) |
|---|---|
| Conventional 2D PAEK | 4100.00 |
| 3D Printed PAEK (SLS) | 2413.77 |
| Conventional 2D PEEK | 3600.00 |
| 3D Printed PEEK (FFF) | 1933.55 |

Table 2 shows the compressive Test Results Comparing Conventionally Manufactured PAEK and PEEK and Their 3D Printed Counterparts. As discussed, the conventional 2D fabricated PAEK and PEEK was produced from a CNC machined bar stock and has a much higher compressive strength than the 3D printed PAEK and PEEK test structures.

Figure 7:
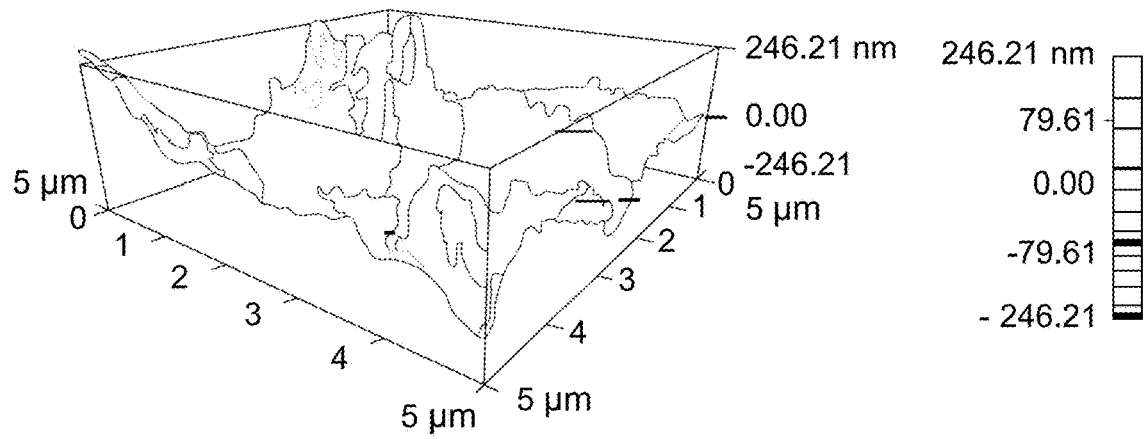
FIG. 7 illustrates an AFM analysis of 2D fabricated and machined PEEK polymers before lipase etching.
Figure 8:
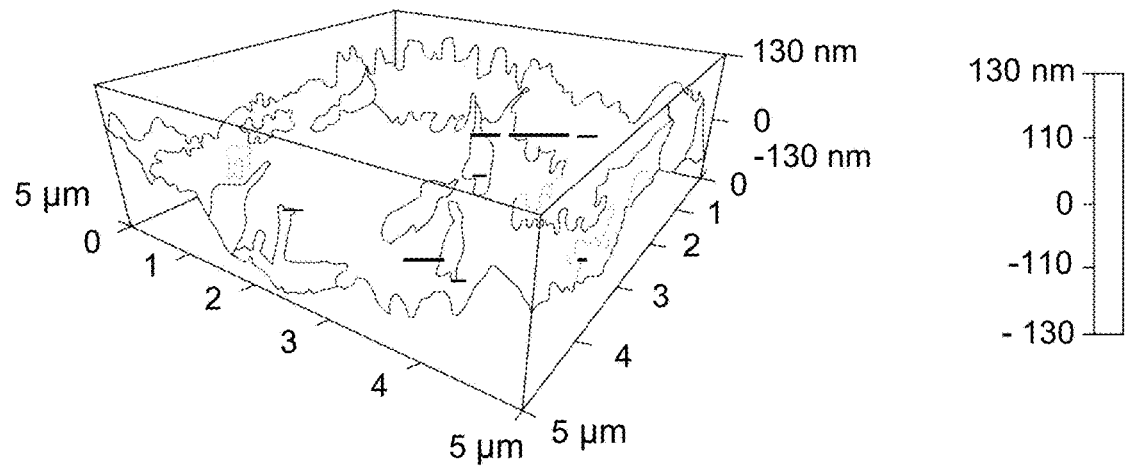
FIG. 8 illustrates an AFM analysis of 2D fabricated and machined PEEK polymers after lipase etching. Note the increased roughness after lipase treatment and the less increase in roughness compared to 3D printed FFF PEEK before and after lipase treatment (FIGS. 3 to 4).
Figure 9:
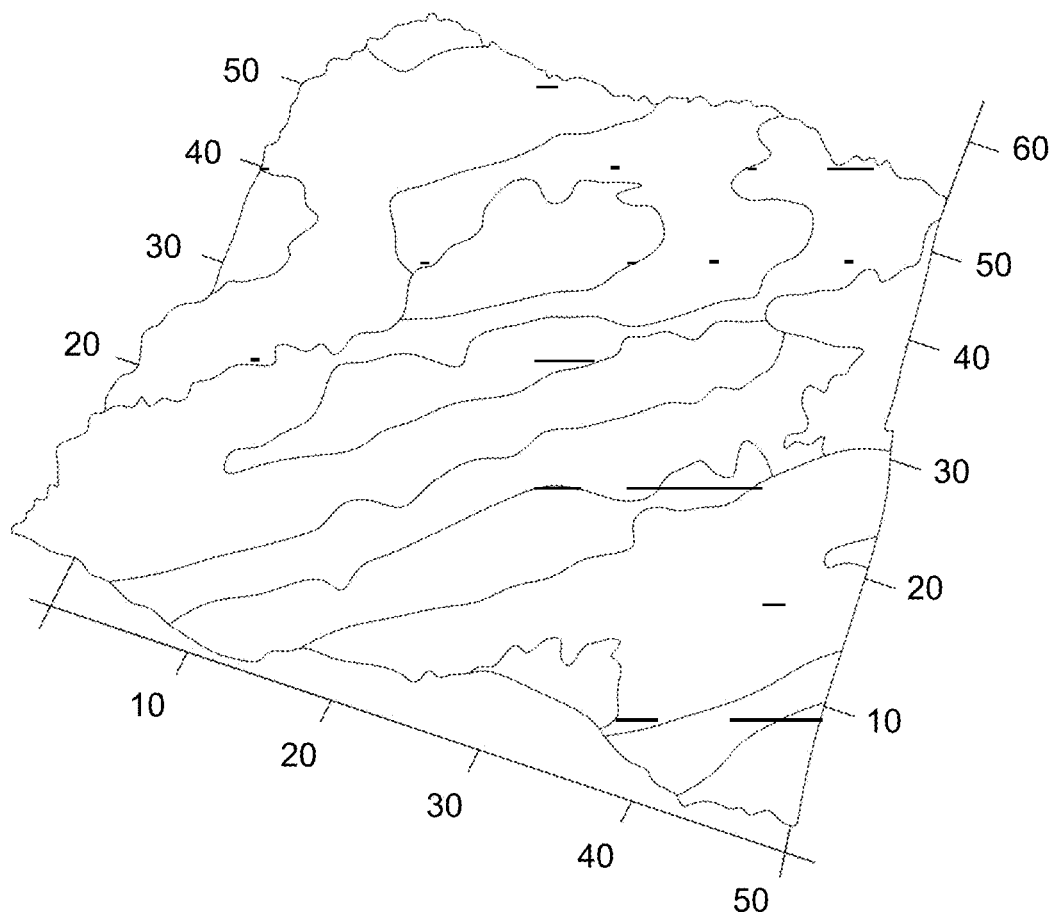
FIG. 9 illustrates an AFM analysis of a smooth surface of a traditional 2D fabricated PEEK polymers.

FIGS. 1, 3, 5, and 7 illustrate AFM analysis of the 3D printed polymers before lipase etched and FIGS. 2, 4, 6, and 8 illustrate AFM analysis of the 3D printed polymers after being lipase etched with increased surface roughness. FIG. 9 shows a traditional 2D manufactured PEEK AFM. The AFM surface roughness measurements are recorded in RMS-root mean square roughness (nm).

Figure 2:
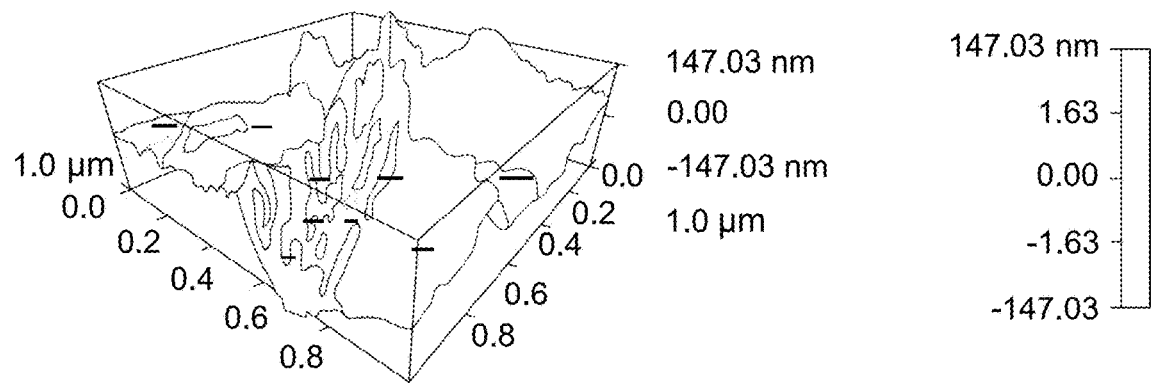
FIG. 2 illustrates an AFM analysis of SLS 3D printed PEEK polymers after lipase etching. Note the increased roughness after lipase treatment.

FIG. 1 illustrates an AFM analysis of a SLS 3D printed PEEK polymer test sample before lipase etching with a measured RMS surface roughness of 33.01 nm. FIG. 2 illustrates an AFM analysis of the SLS 3D printed PEEK polymer test sample after lipase etching with a measured RMS surface roughness of 63.05 nm. In this example, the lipase etching has increased the RMS surface roughness by 30.04 nm.

Figure 3:
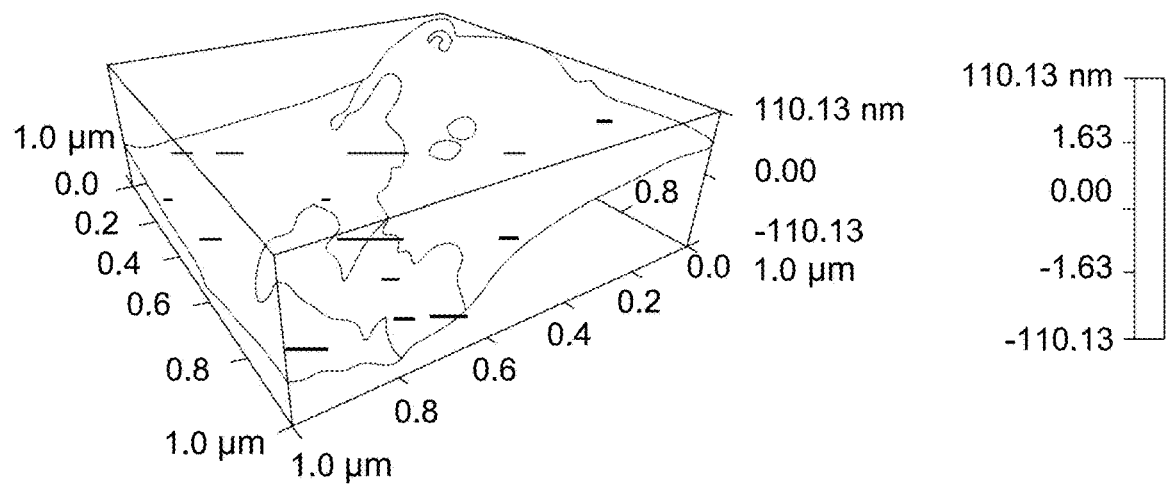
FIG. 3 illustrates an AFM analysis of FFF 3D printed PEEK polymers before lipase etching.
Figure 4:
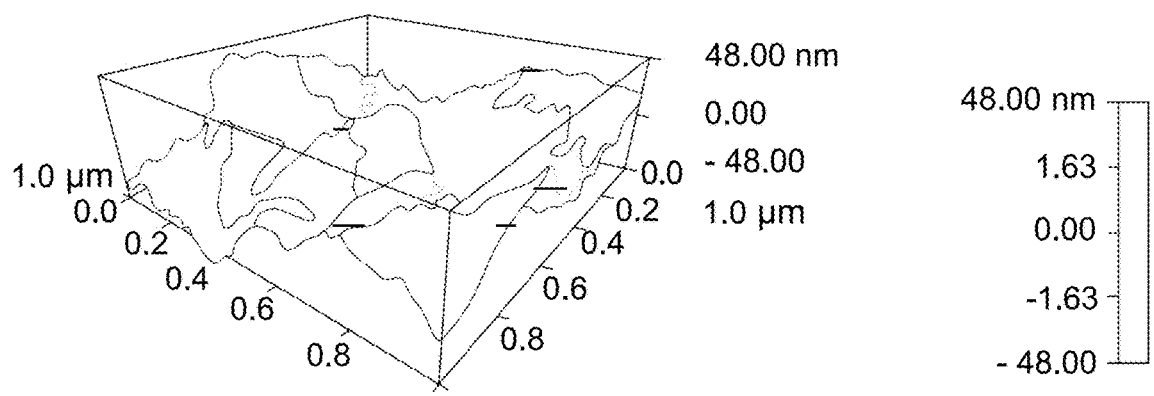
FIG. 4 illustrates an AFM analysis of FFF 3D printed PEEK polymers after lipase etching. Note the increased roughness after lipase treatment.

FIG. 3 illustrates an AFM analysis of an FFF 3D printed PEEK polymer test sample before lipase etching with a measured RMS surface roughness of 13.09 nm. FIG. 4 illustrates an AFM analysis of the FFF 3D printed PEEK polymer test sample after lipase etching with a measured RMS surface roughness of 113.09 nm. In this example, the lipase etching has increased the RMS surface roughness by 100.0 nm or one order of magnitude (10×).

Figure 5:
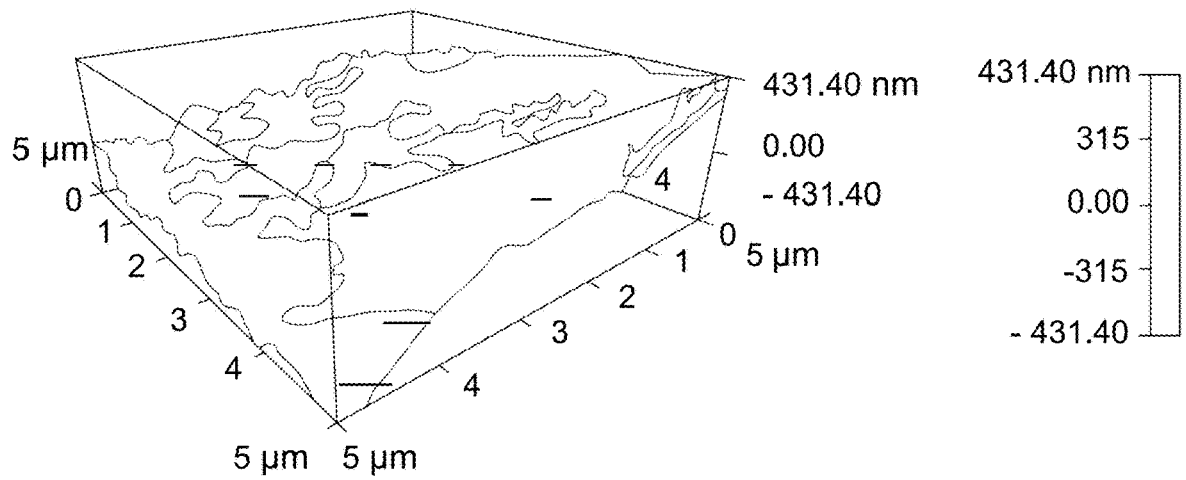
FIG. 5 illustrates an AFM analysis of SLS 3D printed PAEK polymers before lipase etching.
Figure 6:
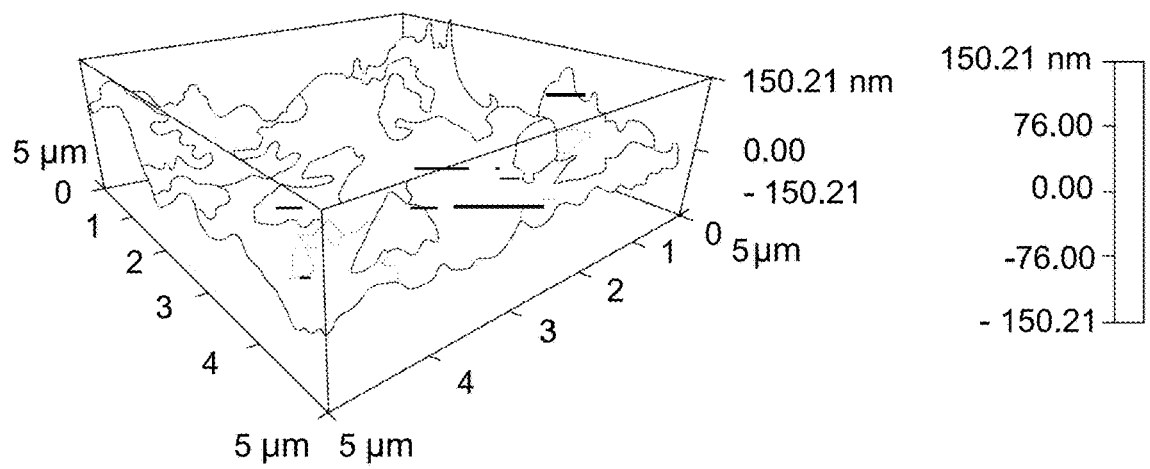
FIG. 6 illustrates an AFM analysis of SLS 3D printed PAEK polymers after lipase etching. Note the increased roughness after lipase treatment.

FIG. 5 illustrates an AFM analysis of an SLS 3D printed PAEK polymer test sample before lipase etching with a measured RMS surface roughness of 26.81 nm. FIG. 6 illustrates an AFM analysis of the SLS 3D printed PAEK polymer test sample after lipase etching with a measured RMS surface roughness of 132.55 nm. In this example, the lipase etching has increased the RMS surface roughness by 105.74 nm.

FIG. 7 illustrates an AFM analysis of a 2D fabricated and machined PEEK polymer test sample before lipase etching with a measured RMS surface roughness of 42.1 nm. FIG. 8 illustrates an AFM analysis of 2D fabricated and machined PEEK polymer test sample after lipase etching with an RMS surface roughness of 148.76 nm. In this example, the lipase etching has increased the RMS surface roughness by 106.66 nm or by a factor of 3.5× which is less than the one order of magnitude (10×) achieved above on FFF 3D printed PEEK.

FIG. 9 illustrates an AFM analysis of the traditional 2D PEEK test sample without any lipase etching with an RMS surface roughness of 4.024 nm. Note that this RMS surface roughness is significantly smaller than the RMS roughness of any of the 3D printed polymer test sample before lipase etching described above in FIGS. 1, 3, and 5. When comparing FIGS. 1, 3, and 5 to FIG. 9, it is clear that the 3D printed polymers were much rougher and have much greater surface areas than the conventional 2D machine fabricated polymer (specifically going from 4.024 nm to as high as 148.76 nm in RMS). Moreover, it is further clear that roughness and thus surface area increased after lipase treatment (specifically going from doubling for SLS 3D Printed PEEK to almost one order of magnitude (10×) for Machined 3D Printed PEEK). It is expected that this change in roughness and surface area led to an increased exposure of material which led to the observed differences in surface energy and interaction with key proteins that inhibit bacteria (mucin and casein) and promote osteoblast (vitronectin) function presented in
Table 1.

FIG. 10-13 illustrate XPS analysis graphs of test samples used to measure the chemical compositions of the test samples. From the chemical composition information, it is possible to determine other chemical properties of the test samples such as oxygen/carbon ration (O/C). The O/C ratio is a way to further assess changes in surface energy since oxygen (the numerator) is more charged than carbon (the denominator). Thus, a higher O/C ratio supports higher surface charge. Note the similar chemistry between each 3D printed sample.

Figure 10:
FIG. 10 illustrates an XPS analysis graph of the 3D FFF printed PEEK polymer structure. The atomic percentage of each element found is also given on the spectra.

FIG. 10 illustrates an XPS analysis graph of the 3D FFF printed PEEK test sample. The XPS analysis indicates that the atomic concentrations are: Ca 0.4%, Si 1.3%, C 86.5%, and O 11.8%. The O/C ratio (11.8%/86.5%)=0.136.

Figure 11:
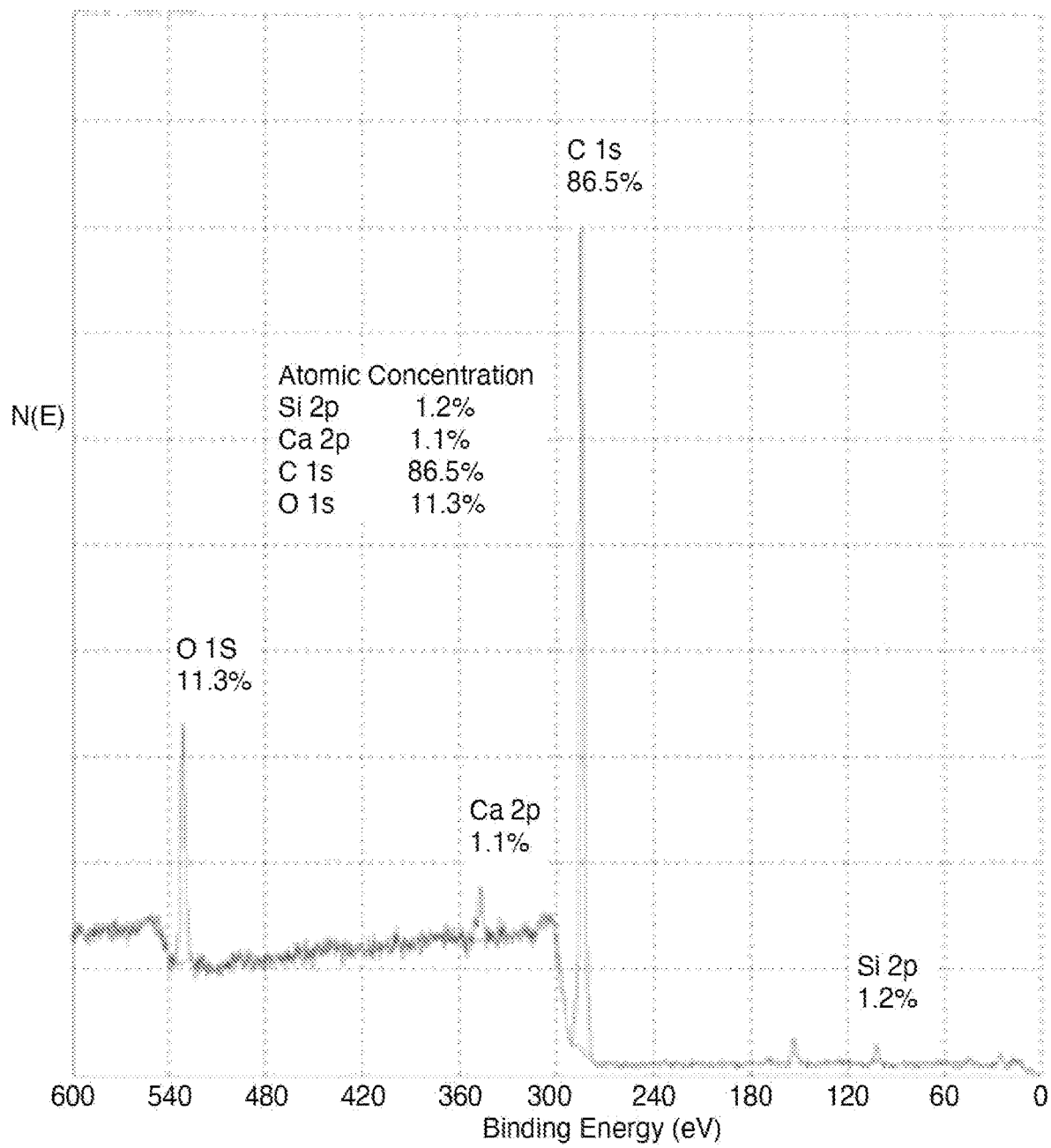
FIG. 11 illustrates an XPS analysis of the traditional 2D manufactured PEEK polymer structure. The atomic percentage of each element found is also given on the spectra.

FIG. 11 illustrates an XPS analysis of the traditional 2D manufactured PEEK. In this example, the PEEK was machined with a CNC machine. The XPS analysis indicates that the atomic concentrations are: Ca 1.1%, Si 1.2%, C 86.5%, and O 11.3%. The O/C ratio (11.3%/86.5%)=0.130.

Figure 12:
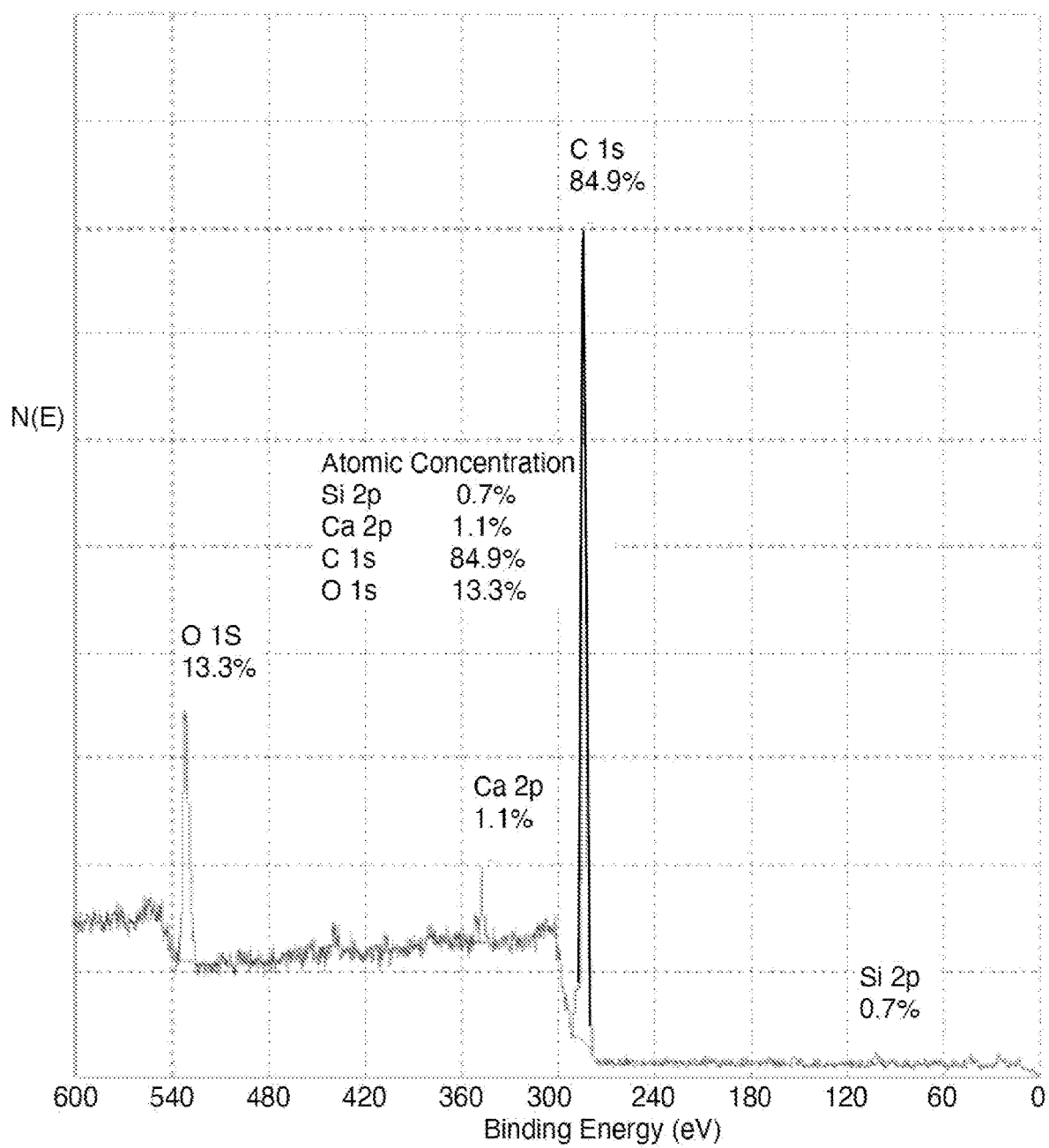
FIG. 12 illustrates an XPS analysis graph of the 3D SLS printed PEEK polymer structure. The atomic percentage of each element found is also given on the spectra.

FIG. 12 illustrates a 3D SLS printed PEEK structure. The XPS analysis indicates that the atomic concentrations are: Ca 1.1%, Si 0.7%, C 84.9%, and O 13.3%. The O/C ratio (13.3%/84.9%)=0.156.

Figure 13:
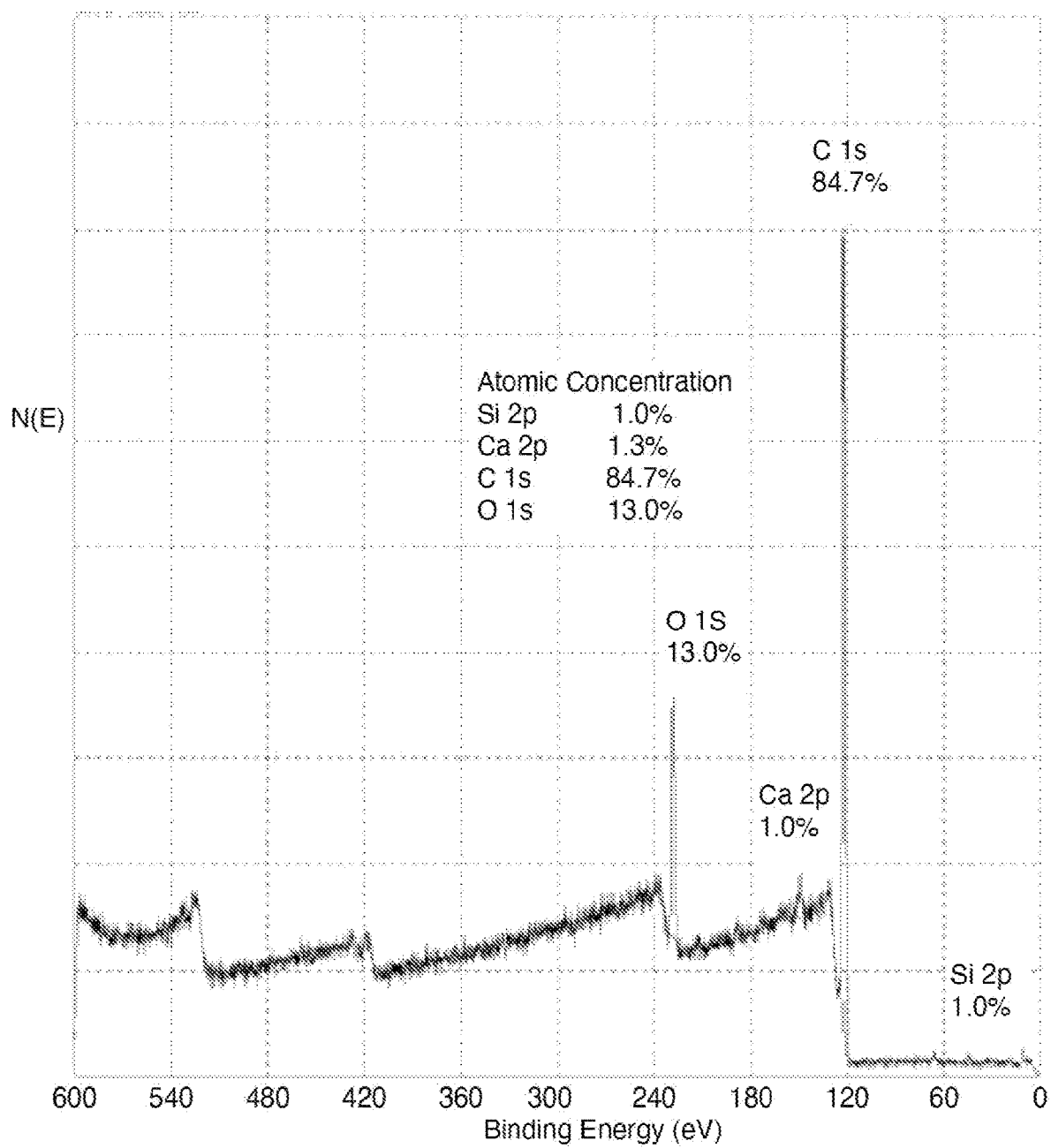
FIG. 13 illustrates an XPS analysis graph of the 3D SLS printed PAEK polymer structure. The atomic percentage of each element found is also given on the spectra.

FIG. 13 illustrates an XPS analysis graph of the 3D SLS printed PAEK polymer test structure. The XPS analysis indicates that the atomic concentrations are: Ca 1.3%, Si 1.0%, C 84.7%, and O 13.0%. The O/C ratio (13.0%/84.7%)=0.153.

Note that the O/C ratio for FFF PEEK was 0.136 (FIG. 10), PEEK Machined was 0.130 (FIG. 11), SLS PEEK was 0.156 (FIG. 12), and PAEK was 0.153 (FIG. 13). Thus, the O/C of the conventional 2D manufactured PEEK was 0.130 which was significantly lower than the 3D printed polymers (ranging from to 0.136 to 0.156). Since a greater O/C ratio means a greater ratio of charged oxygen to uncharged carbon, such results support the above findings of greater surface energy of 3D printed polymers.

Figure 14:
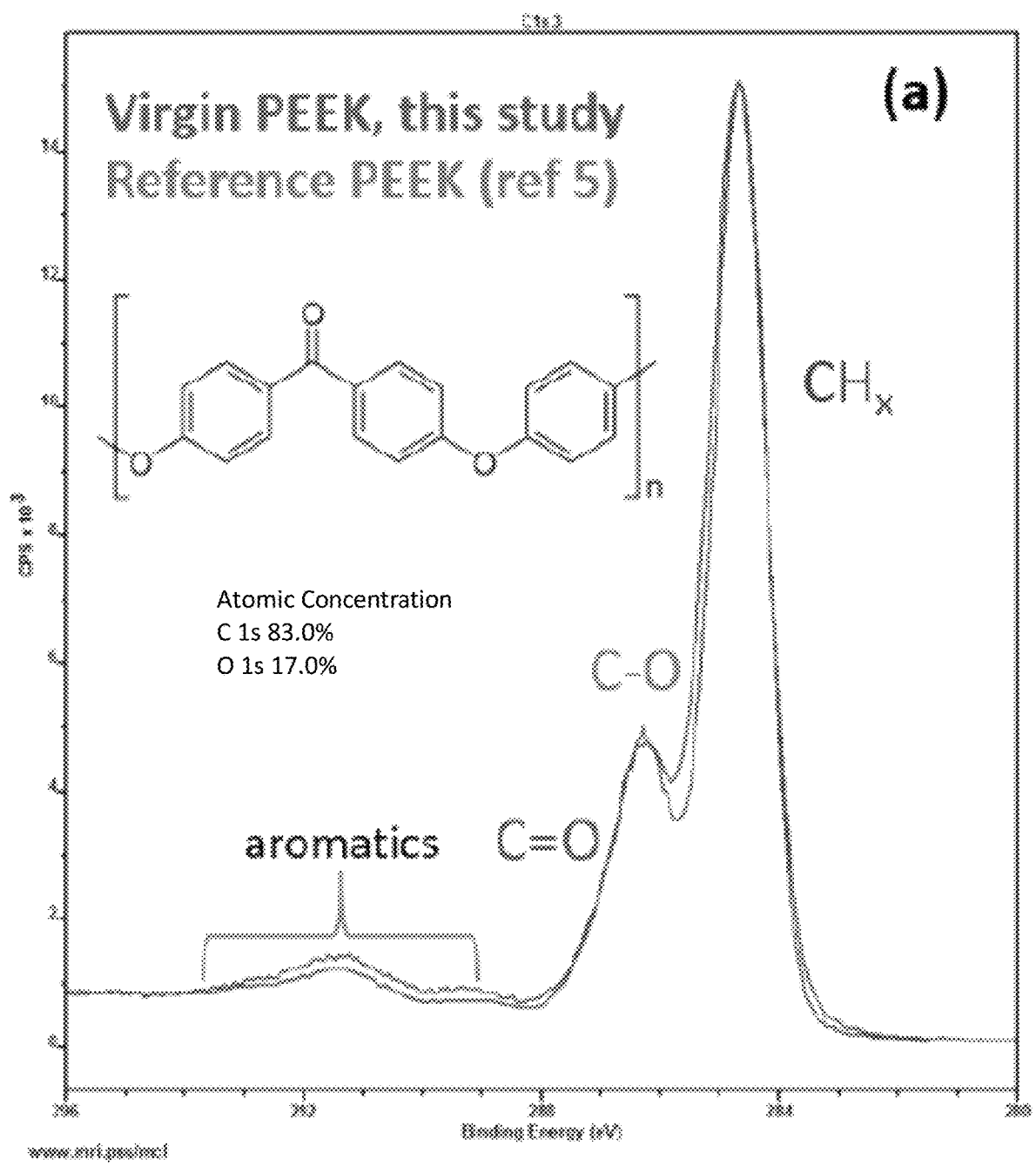
FIG. 14 illustrates an XPS analysis graph of the 3D printed PEEK polymer structure. The atomic percentage of each element found is also given on the spectra.

FIG. 14 illustrates an XPS analysis of the traditional 2D manufactured PEEK test structure. Note the O/C of the conventional 2D manufactured PEEK was 0.16 which was significantly different than the 3D printed polymers (ranging from to 0.13 to 0.15) and the traditional 2D manufactured PEEK did not contain calcium as the 3D printed samples did as evidenced by a lack of calcium peak in the XPS scan.

As shown in FIGS. 10-13, it is clear that all of the 3D printed and 3D manufactured polymers (as well as 2D machined PEEK) possessed calcium, carbon and oxygen, yet from FIG. 14, it is clear that the conventional 2D sample possessed only carbon and oxygen and do not include calcium. Since calcium is highly charged, these results show why the 3D printed polymers had higher surface energy that the traditional 2D sample.

These changes in chemical composition, as well as changes in oxygen/carbon ratios and present of calcium can result in differences in surface energy and interaction with key proteins that inhibit bacteria (mucin and casein) and promote osteoblast (vitronectin) function as presented in Table 1. For example, many of these proteins (specifically, vitronectin) have calcium binding sites, thus, an increase in calcium can lead to an increase in vitronectin adsorption in implantable devices having a chemical composition that includes calcium.

Figure 15:
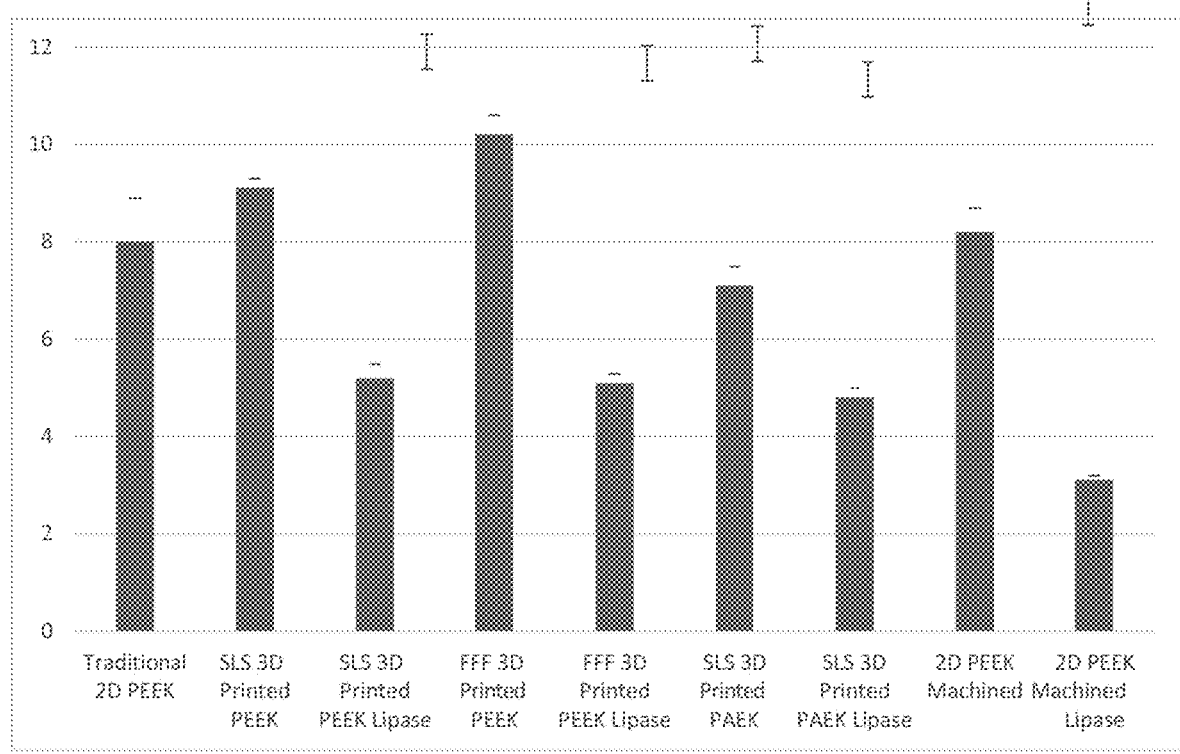
FIG. 15 illustrates decreased MRSA colonization on respective lipase to non-lipase treated 3D printed and 2D manufactured samples after 24 hours. Further, MRSA colonization was less on 3D printed SLS PAEK compared to traditional 2D manufactured PEEK and 2D manufactured PEEK. Data=mean+/−SEM; N=3. Statistical (p<0.01) groups include less MRSA colonization on all lipase treated polymers and 3D printed SLS PAEK compared to all others.

FIG. 15 is a graph showing the MRSA colonization on 3D printed and 2D fabricated polymer test samples with and without lipase etching. The test samples were exposed to an MRSA seeding density=$10^6$ CFU/ml and N=3.

The MRSA colonization of the 3D SLS printed PEEK test samples without lipase etching was 9.1 CFU×$10^6$/ml and about 5.2 CFU×$10^6$/ml with lipase etching. The MRSA colonization of the 3D FFF printed PEEK test samples without lipase etching was 10.2 CFU×$10^6$/ml and about 5.1 CFU×$10^6$/ml with lipase etching. The MRSA colonization of the 3D printed PAEK test samples without lipase etching was 7.1 CFU×$10^6$/ml and about 4.8 CFU×$10^6$/ml with lipase etching. The MRSA colonization of the 2D machined PEEK without lipase etching was 8.2 CFU×$10^6$/ml and about 3.1 CFU×$10^6$/ml with lipase etching. In all test samples, MRSA colonization decreased (p<0.01) on the lipase etched 3D printed and 2D manufactured polymer test samples compared to the 3D printed and 2D manufactured polymer test samples controls that were not lipase etched. As a comparison, 8×$10^6$ MRSA colonized the traditionally prepared 2D PEEK under the same conditions and time period which was significantly greater than the SLS 3D printed PAEK and all lipase treated samples.

Figure 16:
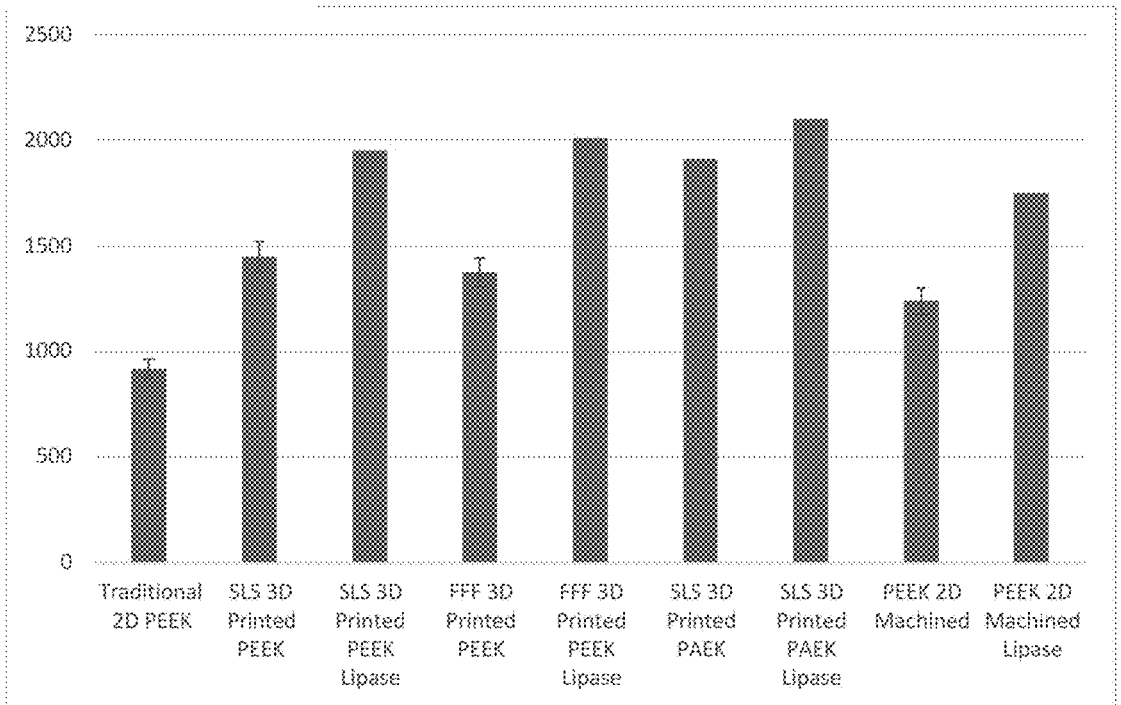
FIG. 16 illustrates increased osteoblast adhesion on respective lipase to non-lipase treated 3D printed and 2D manufactured samples after 4 hours. Further, osteoblast was greater on 3D printed compared to respective 2D polymers. Data=mean+/−SEM; N=3. Statistical (p<0.01) groups include more osteoblast adhesion on all lipase compared to respective non-lipase treated polymers and 3D printed compared to all respective 2D polymers.

FIG. 16 is a graph illustrating osteoblast density on 3D printed and 2D fabricated polymer test samples with and without lipase etching. The osteoblast seeding density=2, 500 cells/cm$^2$ and N=3. In all test samples, the osteoblast adhesion increased on the lipase etched 3D printed polymers. The osteoblast densities on the lipase treated 3D printed polymers are significantly (p<0.01) more than respective untreated polymers. In this graph, the PEEK Machined was CNC prepared 3D PEEK. As a comparison, 920 osteoblasts/square cm adhered to the traditionally prepared 2D PEEK under the same conditions and time period.

The inventive implant structures that have been 3D printed and lipase etched can inhibit implant infection without contributing to antibiotic resistance. The test results above show the ability to use lipase treatment to create 3D printed implant structures having a surface energy closer to endogenous proteins known to reduce MRSA colonization (casein=48 mN/m, mucin=42-46 mN/m, and lubricin=40 mN/m). Thus, by modifying implant surface properties to reduce MRSA colonization, the chances of implant infection are drastically reduced. Fewer MRSA attachment to an implant surface can decrease MRSA growth on a 3D printed implant surface and enable the natural immune system to clear those MRSA that did not attach to the surface. This reduction in MRSA colonization is not currently accomplished with traditional 2D manufactured implants. Furthermore, this reduced MRSA colonization was accomplished without using antibiotics and, thus, this approach does not contribute to the potential growth of antibiotic resistant bacteria that may not be able to be killed through the use of antibiotics. This method for reducing infections can be much better for the health of the patient since the mechanism for reducing bacteria colonization is based upon surface energy and not dependent on any antibiotics. The described lipase exposure to 3D printed implantable devices can also decrease the colonization of other bacteria such as *E. coli*, *Pseudomonas aeruginosa*, Staph. epidermidis, P. acne, Staph. *aureus*, MRSE, MDR *E. coli*, *Candida albicans*, gram positive bacteria including: *Pseudomonas*, *Klebsiella*, *Proteus*, *Salmonella*, *Providencia*, *Escherichia*, *Morganella*, *Aeromonas*, and *Citrobacter* and gram negative bacteria including: staphylococci ("staph"), streptococci ("strep"), pneumococci, and the bacterium responsible for diphtheria (*Corynebacterium diphtheriae*) and anthrax (*Bacillus anthracis*).

Another novel application of using lipase exposure to change the surface energy of 3D printed implantable materials is to reduce inflammation. Inflammation may create a prolonged soft tissue formation surrounding an orthopedic implant inhibiting proper bone fixation for implant success. For example, IgG is a well known antibody that attaches to an implant surface to indicate to immune cells to identify and remove a foreign material. IgG also has a surface energy around 42.5 mN/m and thus the adsorption (or opsonization) of IgG to a 3D printed material can be controlled by lipase exposure as demonstrated above. A decrease in IgG would decrease inflammation helpful for numerous implants (including not just orthopedic, but vascular, cardiovascular, cartilage, neural, spine, skin, GI tract, catheters, endotracheal tubes, drug delivery needles, etc.). Such approaches could also be used to limit inflammation around sensors formed on implantable devices through lipase exposure.

Yet another novel application of the use of lipase exposure is to deposit nanoparticles in 3D printed materials to improve tissue growth. Lipase exposure can transform the surface energy to be closer to 42.5 mN/m which is closer to proteins that are known to improve tissue growth. For example, both vitronectin having a surface energy of 43 mN/m and fibronectin having a surface energy of 42 mN/m are proteins known to improve tissue growth. These proteins also promote mammalian cell adhesion and subsequent functions (including tissue formation) for numerous other tissues including cartilage, vascular, cardiovascular, nervous system, skin, GI tract, and others. Thus, lipase exposure to materials could be used for numerous other implantable materials to promote such tissue growth. The higher tissue ingrowth can improve the regeneration of bone, cartilage, ligaments, tendons, GI tissue, vascular tissue, cardiovascular tissue, skin, nervous system tissue, spinal tissue, muscle, or any tissue in the body.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The present invention and some of its advantages have been described in detail for some embodiments. It should be understood that although the process is described with reference to a device, system, and method the process may be used in other contexts as well. It should also be understood that various changes, substitutions and alterations can be made herein without departing from the spirit and scope of the invention as defined by the appended claims. An embodiment of the invention may achieve multiple objectives, but not every embodiment falling within the scope of the attached claims will achieve every objective. Moreover, the scope of the present application is not intended to be limited to the particular embodiments of the process, machine, manufacture, composition of matter, means, methods and steps described in the specification. A person having ordinary skill in the art will readily appreciate from the disclosure of the present invention that processes, machines, manufacturing steps, compositions of matter, means, methods, or steps, presently existing or later to be developed are equivalent to, and fall within the scope of, what is claimed. Accordingly, the appended claims are intended to include within their scope such processes, machines, manufacturing steps, compositions of matter, means, methods, or steps.

What is claimed is:

1. A method for creating a 3D printed implantable device having a surface that promotes bone ingrowth and inhibits infection comprising:
   a. fusing a plurality of parallel planar layers of material to fabricate the 3D printed implantable device;
   b. exposing the 3D printed implantable device to a lipase solution consisting of lipase and water to etch a nanoparticle layer on the surface of the 3D printed implantable device having nanoscale surface features that increase a surface area of the 3D printed implantable device and increase the surface energy of the surface of the 3D printed implantable device; and
   c. rinsing the 3D printed implantable device with an acetone cleaning solution to stop the etching of the 3D printed implantable device by the lipase solution.

2. The method of claim 1 wherein a concentration of lipase in the lipase solution is between 0.05-0.20 mg/ml.

3. The method of claim 1 wherein a concentration of lipase in the lipase solution is between 0.01-1.00 mg/ml.

4. The method of claim 1 wherein the surface energy of the 3D printed implantable device is between 35 and 55 millinewton per meter (mN/m) after the 3D printed implantable device has been exposed to the lipase solution.

5. The method of claim 1 wherein the surface roughness of the 3D printed implantable device is between 100 nm and 160 nm (RMS) after the 3D printed implantable device has been exposed to the lipase solution.

6. The method of claim 1 wherein a surface crystallinity of the 3D printed implantable device is altered after the 3D printed implantable device has been exposed to the lipase solution.

7. The method of claim 1 wherein a surface chemistry of the 3D printed implantable device is altered to increase a charged electrons density on the surface of the 3D printed implantable device after the 3D printed implantable device has been exposed to the lipase solution.

8. The method of claim 1 wherein the 3D printed implantable device includes at least one of: a metal, a polymer, or a ceramic.

9. The method of claim 1 wherein a surface chemistry of the implantable device is altered after the exposure to the lipase solution.

10. A method for creating a 3D printed implantable device having a surface that promotes bone ingrowth and inhibits infection comprising:
    a. fusing a plurality of parallel planar layers of material to fabricate the 3D printed implantable device; and
    b. exposing the 3D printed implantable device to a lipase solution consisting of lipase and water to etch a nanoparticle layer on the surface of the 3D printed implantable structure having nanoscale surface features that increase a surface roughness of the 3D printed implantable device between 100 nm and 160 nm (RMS) after the 3D printed implantable device has been exposed to the lipase solution.

11. The method of claim 10 wherein a concentration of lipase in the lipase solution is between 0.05-0.20 mg/ml.

12. The method of claim 10 wherein a concentration of lipase in the lipase solution is between 0.01-1.00 mg/ml.

13. The method of claim 10 wherein the surface energy of the 3D printed implantable device is between 35 and 55 millinewton per meter (mN/m) after the 3D printed implantable device has been exposed to the lipase solution.

14. The method of claim 10 wherein a surface crystallinity of the 3D printed implantable device is altered after the 3D printed implantable device has been exposed to the lipase solution.

15. The method of claim 10 wherein a surface chemistry of the 3D printed implantable device is altered to increase a charged electrons density on the surface of the 3D printed implantable device after the 3D printed implantable device has been exposed to the lipase solution.

16. The method of claim 10 wherein the 3D printed implantable device includes at least one of: a metal, a polymer, or a ceramic.

17. The method of claim 10 wherein a surface chemistry of the 3D printed implantable device is altered after the exposure to the lipase solution.

* * * * *